(12) United States Patent
Burnett

(10) Patent No.: US 8,658,101 B1
(45) Date of Patent: Feb. 25, 2014

(54) PHOTOCATALYTIC DEVICE WITH CURVED REFLECTORS

(75) Inventor: Gregg William Burnett, Royse City, TX (US)

(73) Assignee: Dust Free, LP, Royse City, TX (US)

( * ) Notice: Subject to any disclaimer, the term of this patent is extended or adjusted under 35 U.S.C. 154(b) by 0 days.

(21) Appl. No.: 13/353,419

(22) Filed: Jan. 19, 2012

(51) Int. Cl.
*A61L 2/10* (2006.01)

(52) U.S. Cl.
USPC .............................................. 422/121; 422/24

(58) Field of Classification Search
USPC ................................................... 422/121, 24
See application file for complete search history.

(56) References Cited

U.S. PATENT DOCUMENTS

| | | |
|---|---|---|
| 4,859,329 A | 8/1989 | Fink |
| 5,011,609 A | 4/1991 | Fink |
| 5,120,435 A | 6/1992 | Fink |
| 5,236,585 A | 8/1993 | Fink |
| 5,919,422 A | 7/1999 | Yamanaka et al. |
| 6,221,314 B1* | 4/2001 | Bigelow .......................... 422/24 |
| 6,531,100 B1* | 3/2003 | Ogata et al. .................... 422/177 |
| 6,546,883 B1 | 4/2003 | Fink et al. |
| 6,730,265 B2* | 5/2004 | Horton, III ...................... 422/24 |
| 6,752,970 B2 | 6/2004 | Schwartz et al. |
| 6,784,440 B2 | 8/2004 | Fink et al. |
| 6,949,228 B2 | 9/2005 | Ou Yang et al. |
| 6,997,185 B2 | 2/2006 | Han et al. |
| 7,160,566 B2 | 1/2007 | Fink et al. |
| 7,635,659 B2 | 12/2009 | Naganuma et al. |
| 7,871,518 B2 | 1/2011 | Ellis et al. |
| 7,988,923 B2 | 8/2011 | Fink et al. |
| 2003/0077211 A1 | 4/2003 | Schwartz et al. |
| 2003/0150708 A1 | 8/2003 | Fink |
| 2003/0230477 A1 | 12/2003 | Fink et al. |
| 2004/0016887 A1 | 1/2004 | Fink et al. |
| 2004/0056201 A1 | 3/2004 | Fink et al. |
| 2004/0156959 A1 | 8/2004 | Fink et al. |
| 2004/0197243 A1 | 10/2004 | Schwartz et al. |
| 2005/0186124 A1 | 8/2005 | Fink et al. |
| 2005/0238551 A1* | 10/2005 | Snyder et al. .............. 422/186.3 |
| 2006/0144690 A1 | 7/2006 | Fink et al. |
| 2006/0163135 A1* | 7/2006 | Ellis et al. ...................... 210/251 |
| 2006/0228275 A1 | 10/2006 | Rutman et al. |
| 2006/0266221 A1 | 11/2006 | Fink et al. |
| 2007/0110860 A1 | 5/2007 | Fink et al. |
| 2008/0093210 A1* | 4/2008 | Edwards ..................... 204/157.3 |
| 2009/0183943 A1 | 7/2009 | Leistner et al. |
| 2009/0217690 A1 | 9/2009 | Silderhuis |
| 2011/0250125 A1 | 10/2011 | Fink et al. |

FOREIGN PATENT DOCUMENTS

| | | |
|---|---|---|
| CN | 2392106 Y | 8/2000 |
| CN | 2922905 Y | 7/2007 |
| CN | 101245939 A | 8/2008 |
| CN | 201135626 Y | 10/2008 |
| DE | 20211178 U1 | 11/2002 |
| WO | WO 2006/134149 A1 | 12/2006 |

* cited by examiner

*Primary Examiner* — Sean E Conley
*Assistant Examiner* — Donald Spamer
(74) *Attorney, Agent, or Firm* — Fogarty, L.L.C.

(57) ABSTRACT

A photocatalytic device has an ultraviolet light source and a plurality of photocatalytic structures, such as hydrated quad-metallic catalyst surfaces. The photocatalytic device has curved reflectors that are positioned to reflect ultraviolet light against a face of the photocatalytic structures. The curved reflectors are shaped to minimize the distance traveled by the ultraviolet light between the light source and the photocatalytic structure. The curved reflector is further shaped to direct reflected ultraviolet against the surface of the photocatalytic structure in a perpendicular direction.

18 Claims, 4 Drawing Sheets

PHOTOCATALYTIC DEVICE WITH CURVED REFLECTORS

TECHNICAL FIELD

Embodiments of the invention are directed, in general, to oxidation technology for air purification systems and, more specifically, to an efficient system for distributing ultraviolet light to a photocatalyst.

BACKGROUND

Ultraviolet light can be used in heating, ventilation, and air conditioning (HVAC) systems to significantly reduce the amount of microbials in ductwork and air space, which helps to reduce possible health problems associated with inhaling microbials. Ultraviolet light is also beneficial in keeping HVAC coils free of mold, which increases system efficiency.

Ultraviolet (UV) light represents the frequency of light between 185 nanometers (nm) and 400 nm and is invisible to the naked eye. Within the UV spectrum lie three distinct bands of light: UV-A, UV-B, and UV-C. Longwave UV light (315 nm to 400 nm) or UV-A refers to what is commonly called "black light." UV-B (280 nm to 315 nm) or midrange UV is the type of light that causes sunburn. Germicidal UV light (185 nm to 280 nm) or UV-C is effective in microbial control. Research has demonstrated that UV light between 254 nm and 265 nm is most efficient for microbial destruction. Germicidal lamps that produce the majority of their output in this range are the most effective in microbial control and destruction.

A typical HVAC system is used to maintain indoor air quality; however, the primary function of most HVAC systems is to control the temperature and humidity of the air. Many indoor air pollutants, such as volatile organic compounds (VOCs), cannot be removed by typical HVAC systems. Often, an air cleaning device may be added to HVAC systems to remove these VOCs. Photocatalytic air cleaning devices are a common technique for indoor air purification and deodorization. A photocatalytic air cleaning device in a HVAC system typically comprises an ultraviolet lamp that illuminates a photocatalytic filter to create free radicals that eliminate VOCs.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a photocatalytic device comprises an ultraviolet light source and one or more catalyst substrates that are adapted to support a hydroxyl radical reaction with water vapor that results in hydro peroxides and hydroxyl ions. One or more convex reflectors are positioned adjacent to the one or more catalyst substrates. Each of the convex reflectors has a shape that is adapted to distribute reflected light from the ultraviolet light source across a near surface of a catalyst substrate. The catalyst substrates comprise a hydrated quad-metallic catalyst or any other appropriate catalyst.

In another embodiment, one or more additional convex reflectors are positioned adjacent to a far side of the one or more catalyst substrates. Each of the additional convex reflectors having a shape adapted to uniformly distribute reflected light from the ultraviolet light source across the far surface of a catalyst substrate.

In various embodiments, the convex reflectors may have a curved shape of any appropriate radius or a bent shape (i.e. a flat reflector bent into a convex shape). The shape of the convex reflectors is selected to minimize a distance between the ultraviolet light source and the surface of a catalyst substrate.

BRIEF DESCRIPTION OF THE DRAWINGS

Figure 1:
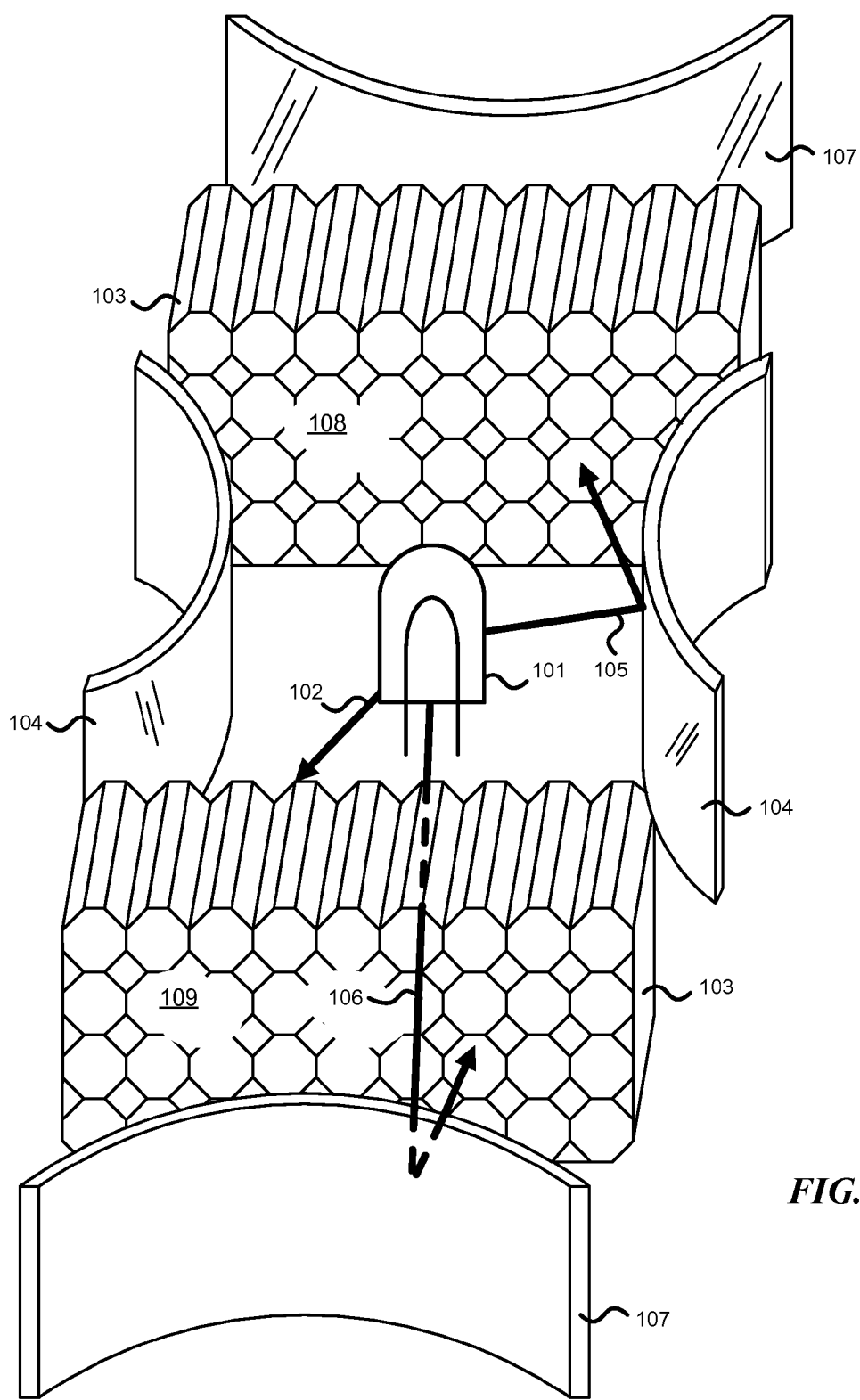
Figure 2:
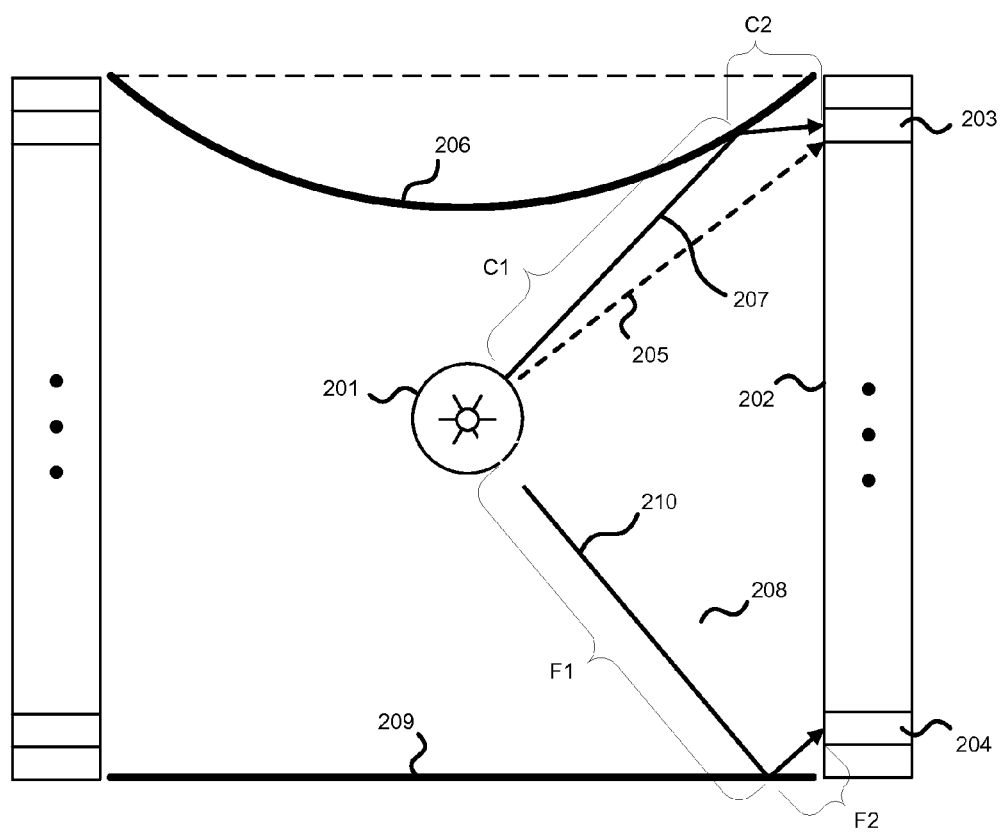
Figure 3:
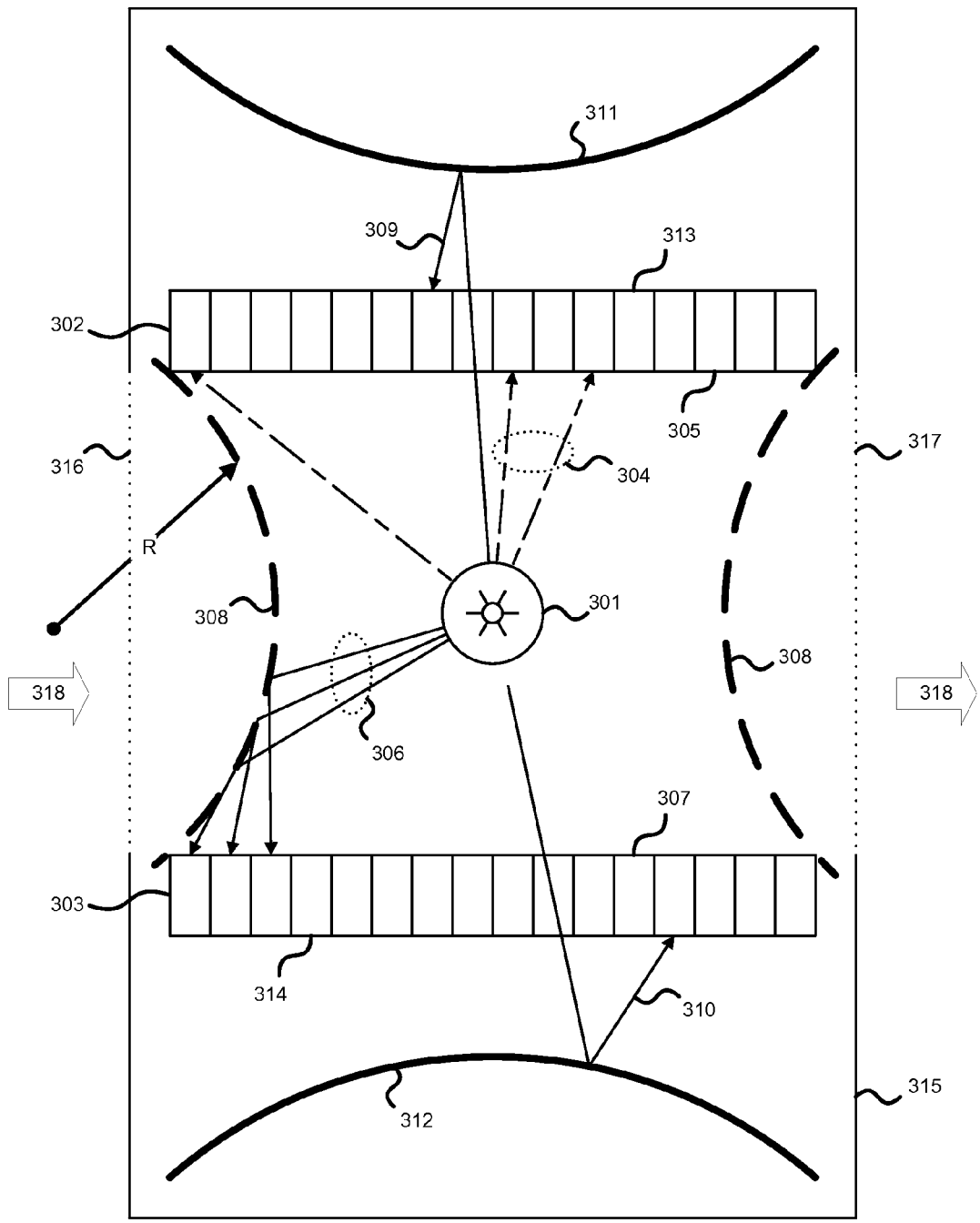
Figure 4:
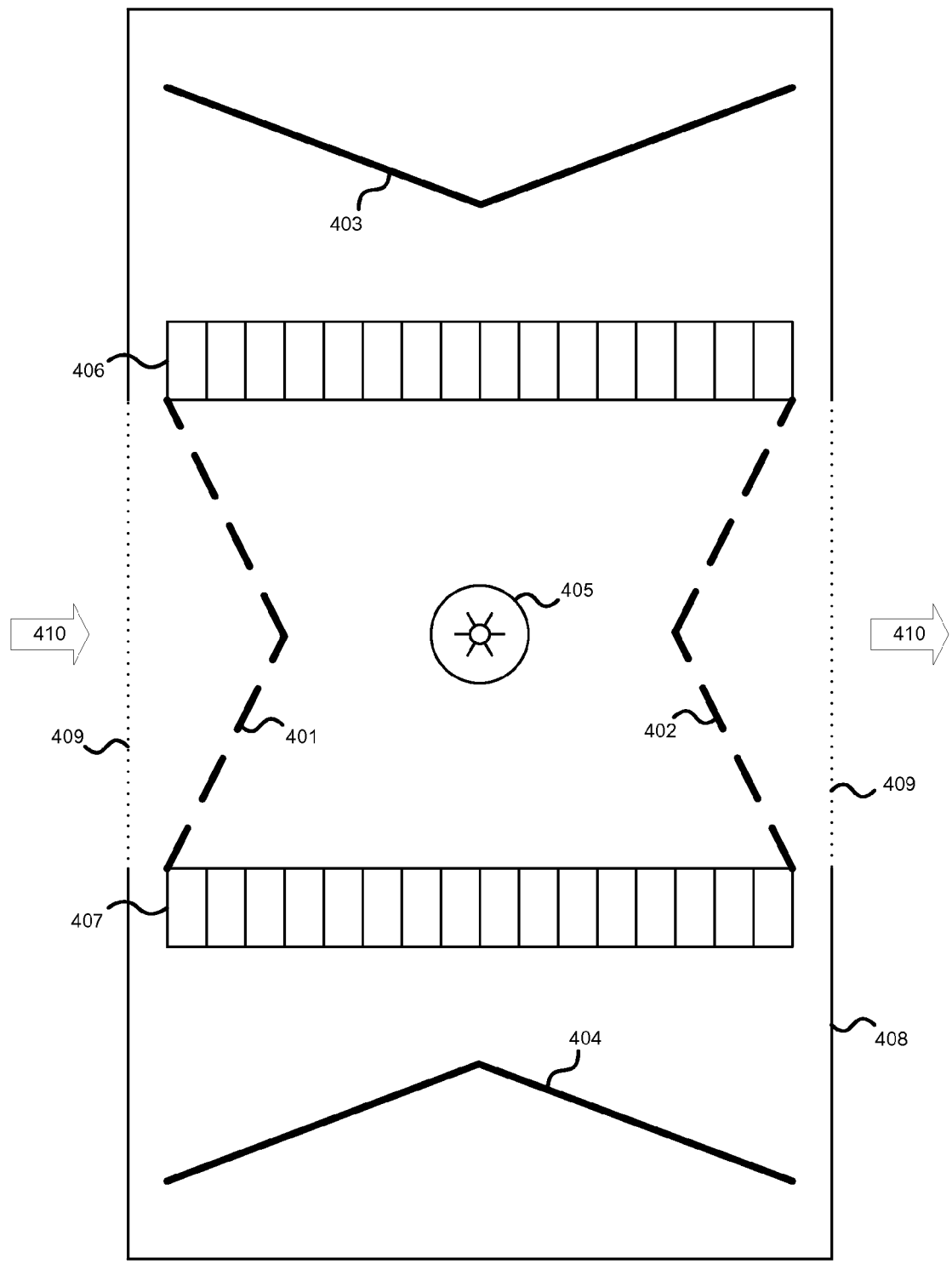

Having thus described the invention in general terms, reference will now be made to the accompanying drawings, which are not necessarily drawn to scale, and wherein:

FIG. 1 is a block diagram illustrating one embodiment of a photocatalytic device;

FIG. 2 is a block diagram illustrating advantages of a curved reflector as used in embodiments of the photocatalytic device described herein;

FIG. 3 is a block diagram illustrating the illumination of opposed surfaces of a target structure according to one embodiment; and FIG. 4 is a block diagram illustrating an alternative embodiment of a photocatalytic device.

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

FIG. 1 is a block diagram illustrating one embodiment of a photocatalytic device. An ultraviolet light source 101 generates ultraviolet light 102. One or more photocatalytic structures 103 are positioned near ultraviolet light source 101 and are illuminated by the ultraviolet light 102. In one embodiment, the photocatalytic structures 103 are comprised of a plurality of fluted structures arranged in a honeycomb formation.

The photocatalytic structures 103 may be, for example, a hydrated catalytic matrix, such as a hydrated quad-metallic catalyst. When the ultraviolet light 102 impacts the photocatalytic structures 103, ozone is produced in the catalytic matrix. The catalyst supports a hydroxyl radical reaction with water vapor that results in hydro peroxides, hydroxyl ions, super oxide ions, passive negative ions hydroxides, and ozonide ions. These are highly reactive chemical species. The hydroxyl radicals are very strong oxidizers and will attack organic materials. This creates oxidation that helps to reduce odors, volatile organic compounds (VOCs), airborne viruses, bacteria, mold and other types of air pollution. The quad-metallic catalytic matrix may be comprised of Rhodium, Titanium, Silver and Copper for example. In other embodiments, other combinations of rare and noble metals may be used for the catalytic matrix.

Ultraviolet light source 101 may be, for example, a high-intensity, broad-spectrum ultraviolet bulb or tube. In other embodiments, the ultraviolet source may be a low pressure fluorescent quartz bulb or a medium pressure amalgam lamp. Ultraviolet light falls in the band of light between 185 nm and 400 nm. There are three distinct bands of light within the ultraviolet spectrum: UV-A, UV-B, and UV-C. Longwave UV light (315 nm to 400 nm), or UV-A, refers to what is commonly called "black light." Midrange UV (280 nm to 315 nm), or UV-B, causes sunburn. Germicidal UV light (185 nm to 280 nm), or UV-C, is effective in microbial control. Research has demonstrated that the most efficient frequency for microbial destruction is between 254 nm and 265 nm within the UV-C band. Germicidal lamps that produce the majority of their output in this range will be the most effective in microbial control/destruction.

One or more curved reflectors 104 are positioned to reflect ultraviolet light 105 from ultraviolet light source 101 to the face 108 of photocatalytic structures 103. As a result, photocatalytic structures 103 receive both direct ultraviolet light from source 101 and reflected ultraviolet light 105 from curved reflectors 104.

Some ultraviolet light 106 passes through photocatalytic structures 103. Additional curved reflectors 107 are positioned so that ultraviolet light 106 is reflected back to photocatalytic structures 103 on the face 109 opposite ultraviolet light source 101.

In one embodiment, reflectors 106 and 107 are curved in a manner that optimizes the distribution of ultraviolet light across the faces 108, 109 of photocatalytic structures 103.

FIG. 2 is a block diagram illustrating advantages of a curved reflector as used in embodiments of the photocatalytic device described herein. The inverse-square law of light results in a rapid drop-off in the intensity of ultraviolet light as it is radiated away from the light source. The intensity of light waves radiating from a light source is inversely proportional to the square of the distance from the light source. This affects the amount of energy provided to surfaces that are illuminated by the light source. For example, a far surface that is twice as far away from a light source as a near surface, receives only one-quarter of the energy that is received by the near surface. Accordingly, it is important to minimize the distance traveled by the ultraviolet light in the photocatalytic device.

Light source 201 that broadcasts light on target surface 202, which includes a plurality of segments 203, 204. Segment 203 receives light directly from source 201, as illustrated by ray 205. Segment 203 also receives light indirectly from source 201 after reflection from curved reflector 206, as illustrated by ray 207. The light 207 reflected off of curved reflector 206 has a total distance C1+C2.

Segment 204 receives light directly from source 201, as illustrated by ray 208. Segment 204 also receives light indirectly from source 201 after reflection from flat reflector 209, as illustrated by ray 210. The light 210 reflected off of flat reflector 209 has a total distance F1+F2. As illustrated in FIG. 2, the distance traveled by ray 210 is longer than the distance traveled by ray 207. Therefore, the ray 207 from curved reflector 206 will have a higher intensity and higher energy level when it reaches segment 203 when compared to the intensity and energy level of ray 210 when it reaches segment 204.

In addition to minimizing the distance traveled by ray 207, curved reflector 206 also causes the reflected ray to impact the target surface 202 in a perpendicular or nearly perpendicular direction. On the other hand, ray 210 reflected off of flat reflector 209 impact the target surface 202 at an acute angle. Where segments 203, 204 are hollow structures, such as fluted segments of a honeycomb substrate, the perpendicular rays 207 will better illuminate the interior of the segment 203 compared to ray 210's illumination of segment 204.

FIG. 3 is a block diagram illustrating the illumination of opposed surfaces of a target structure according to one embodiment. Ultraviolet light source 301 generates broadband ultraviolet light that illuminates target structures 302, 303. Ultraviolet light rays 304 impact a near side 305 of target structure 302. Reflected rays 306 also impact the near side 307 of target structure 303. Reflective surface 308 is shaped to optimize the impact of reflected rays 306 against near surface 307. The curvature R of reflective surface 308 is selected so that reflected rays 306 travel an optimized minimum distance between source 301 and surface 307.

The curvature R of reflective surface 308 may be of a constant radius, such as in a cross-section of a cylindrical surface. In other embodiments, the curvature R of reflective surface 308 may have a variable radius, such as in a cross-section of a paraboloid or ellipsoid. In other embodiments, the curvature of reflective surface 308 has a radius that varies both in a vertical and horizontal direction.

Some ultraviolet light, such as rays 309, 310, may pass through target structures 302, 303 when those structures are comprised of hollow segments. Reflective surfaces 311, 312 reflect rays 309, 310 back against the far surface 313, 314 of the target structures 302, 303. Reflective surfaces 311, 312 are shaped to optimize the impact of reflected rays 3309, 310 against near surface 307. Like surface 308, the curvature of reflective surfaces 311, 312 are selected so that reflected rays 309, 310 travel an optimized minimum distance between source 301 and surfaces 30313, 314. The curvature of reflective surfaces 311, 312 may be of a constant radius or a variable radius and/or a radius that varies both in a vertical and horizontal direction.

The photocatalytic device may include an enclosure 315 that protects and/or supports the components, including ultraviolet source 301, reflectors 308, 311, 312, and target structures 302, 303. Enclosure 315 may include ventilated or perforated sections 316, 317 to allow air (318) to flow through the device. Additionally, reflectors 308 may be ventilated or perforated to allow air to flow through the device, thereby allowing for the distribution of hydro peroxides, hydroxyl ions, or other ions into a ventilation system or room.

FIG. 4 is a block diagram illustrating an alternative embodiment of a photocatalytic device. As illustrated in FIGS. 1-3, the reflectors in the photocatalytic device are generally of a curved, convex shape. FIG. 4 illustrates an alternative reflector configuration in which bent reflectors 401-404 have a convex shape, but the reflectors are not curved. The reflectors 401-404 serve the same purpose as reflectors 308, 311, 312 (FIG. 3) wherein ultraviolet light from source 405 is reflected against the surfaces of target structures 406, 407.

Bent reflectors 401-404 may be preferable to curved reflectors under certain manufacturing conditions, for example. The size, shape and angle of bent reflectors 401-404 are selected to optimize the uniform distribution of ultraviolet light across the surfaces of target structures 406, 407. It will be understood that other convex shapes may also be used for the reflectors in other embodiments.

The photocatalytic device may have an enclosure 408 with ventilated sections 409. Additionally, reflectors 401, 402 may be ventilated in order to improve airflow 410 through the photocatalytic device.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

What is claimed is:

1. A photocatalytic device, comprising:
an ultraviolet light source;
first and second catalyst substrates adapted to support a hydroxyl radical reaction with ultraviolet light and water vapor that results in hydro peroxides and hydroxyl ions, the first and second catalyst substrates positioned on opposite sides of the ultraviolet light source such that a near surface of the first catalyst substrate faces a near surface of the second catalyst substrate, the near surfaces of the first and second catalyst substrates including openings to a plurality of fluted structures, the openings disposed in a direct line-of-sight of at least a portion of light emitted by the ultraviolet light source; and
first and second convex reflectors positioned on opposite sides of the ultraviolet light source and between the first and second catalyst substrates, each of the convex reflectors having a convex surface adapted to reflect at least another portion of the light emitted by the ultraviolet light source directly across the openings of the fluted structures of the near surfaces of the first and second catalyst substrates, wherein the convex surfaces of the first and second convex reflectors face each other.

2. The photocatalytic device of claim 1, further comprising:
one or more additional convex reflectors positioned adjacent to a far surface of at least one of the first or second catalyst substrates and in a parallel configuration with respect to the at least one of the first or second catalyst substrates, each of the additional convex reflectors having a convex surface adapted to uniformly distribute reflected light from the ultraviolet light source across the far surface of the at least one of the first or second catalyst substrates.

3. The photocatalytic device of claim 1, wherein the first and second convex reflectors have a curved shape.

4. The photocatalytic device of claim 1, wherein the first and second convex reflectors have a bent shape.

5. The photocatalytic device of claim 1, wherein the shape of the first and second convex reflectors is selected to minimize a distance traveled by ultraviolet light emitted by the ultraviolet light source toward the near surfaces of the first and second catalyst substrates.

6. The photocatalytic device of claim 2, wherein the shape of the one or more additional convex reflectors is selected to minimize a distance traveled by ultraviolet light emitted by the ultraviolet light source toward the far surface of the at least one of the first and second catalyst substrates.

7. The photocatalytic device of claim 1, wherein the first and second catalyst substrates comprise a hydrated quad-metallic catalyst.

8. A photocatalytic device, comprising:
an ultraviolet light source;
a first catalyst substrate and a second catalyst substrate, the first and second catalyst substrates adapted to support a hydroxyl radical reaction with ultraviolet light and water vapor that results in hydro peroxides and hydroxyl ions, the first and second catalyst substrates positioned such that, in a cross-section of the photocatalytic device, the first and second catalyst substrates are in a parallel configuration with respect to each other and a near surface of the first catalyst substrate facing a near surface of the second catalyst substrate, the near surfaces of the first and second catalyst substrates including openings to a plurality of fluted structures, the openings of the fluted structures of the near surface of the first catalyst substrate facing the openings of the fluted structures of the near surface of the second catalyst substrate, the openings to the plurality of fluted structures disposed in a direct line-of-sight of at least a portion of light emitted by the ultraviolet light source; and
a first convex reflector and a second convex reflector positioned such that, in the cross-section of the photocatalytic device, the first and second convex reflectors are in a parallel configuration with respect to each other and in a perpendicular configuration with respect to the first and second catalyst substrates, the first convex reflector adjoining the first and second catalyst substrates and the second convex reflector adjoining the first and second catalyst substrates, the ultraviolet light source centered with respect to: the first catalyst substrate, the second catalyst substrate, the first convex reflector, and the second convex reflector; the first and second convex reflectors having a convex surface adapted to reflect at least another portion of the light emitted by the ultraviolet light source straight across the near surface of at least one of the catalyst substrates, and wherein the convex surfaces of the first and second convex reflectors are positioned toward one another.

9. The photocatalytic device of claim 8, wherein the convex shape is a smooth curve.

10. The photocatalytic device of claim 8, wherein the convex shape is a V shape.

11. The photocatalytic device of claim 8, wherein the shape of the first and second convex reflectors is selected to minimize a distance traveled by ultraviolet light emitted by the ultraviolet light source toward the near surfaces of the first and second catalyst substrates, respectively.

12. The photocatalytic device of claim 8, wherein the first and second catalyst substrates comprise a hydrated quad-metallic catalyst.

13. A method of manufacturing a photocatalytic device, the method comprising:
providing an ultraviolet light source;
providing a first catalyst substrate and a second catalyst substrate, wherein the first and second catalyst substrates are adapted to support a hydroxyl radical reaction with ultraviolet light and water vapor that results in hydro peroxides and hydroxyl ions;
providing a first convex reflector and second convex reflector;
positioning the first and second catalyst substrates such that, in a cross-section of the photocatalytic device, the first and second catalyst substrates are in a parallel configuration with respect to each other and a near surface of the first catalyst substrate faces a near surface of the second catalyst substrate, the near surfaces of the first and second catalyst substrates including openings to a plurality of fluted structures, the openings of the fluted structures of the near surface of the first catalyst substrate facing the openings of the fluted structures of the near surface of the second catalyst substrate;

positioning the first and second convex reflectors such that, in a cross-section of the photocatalytic device, the first and second convex reflectors are in a parallel configuration with respect to each other and in a perpendicular configuration with respect to the first and second catalyst substrates;

positioning the ultraviolet light between the first and second convex reflectors and between the first and second catalyst substrates, wherein the openings to the plurality of fluted structures are disposed in a direct line-of-sight of at least a portion of light emitted by the ultraviolet light source, and wherein the convex reflectors have a convex surface adapted to reflect at least another portion of the light emitted by the ultraviolet light source across the near surface of at least one of the catalyst substrates in a straight line, wherein the convex surfaces of the first and second convex reflectors are disposed nearest each other.

14. The method of claim 13, further comprising:

positioning additional convex reflectors adjacent to a far surface of one or more of the catalyst substrates, wherein each of the additional convex reflectors have a convex surface adapted to uniformly distribute reflected light from the ultraviolet light source across the far surface of one of the catalyst substrates.

15. The method of claim 13, wherein at least one of the convex reflectors has a curved shape.

16. The method of claim 13, wherein at least one of the convex reflectors has a bent shape.

17. The method of claim 13, wherein the shape of the convex reflectors is selected to minimize a distance traveled by ultraviolet light emitted by the ultraviolet light source toward a near surface of at least one of the catalyst substrates.

18. The method of claim 13, wherein the catalyst substrates comprise a hydrated quad-metallic catalyst.

* * * * *